| United States Patent [19] | [11] Patent Number: 5,030,648 |
| Sudilovsky | [45] Date of Patent: Jul. 9, 1991 |

[54] NEW COMBINATION AND METHOD FOR TREATING OBSESSIVE-COMPULSIVE DISORDER, AND MOTOR AND PHONIC TICS IN TOURETTES' SYNDROME USING SUCH COMBINATION

[75] Inventor: Abraham Sudilovsky, Lawrenceville, N.J.

[73] Assignee: E. R. Squibb & Sons, Inc., Princeton, N.J.

[21] Appl. No.: 464,261

[22] Filed: Jan. 12, 1990

[51] Int. Cl.$^5$ .............................................. A61K 31/40
[52] U.S. Cl. ................................................... 514/423
[58] Field of Search ........................................ 514/423

[56] References Cited

U.S. PATENT DOCUMENTS

| 4,046,889 | 9/1977 | Ondetti et al. | 514/493 |
| 4,105,776 | 8/1978 | Ondetti et al. | 514/493 |
| 4,316,906 | 2/1982 | Ondetti et al. | 514/493 |
| 4,337,201 | 6/1982 | Petrillo | 548/413 |
| 4,452,790 | 6/1984 | Karanewsky et al. | 546/22 |

OTHER PUBLICATIONS

Merck Index, 10th Ed., p. 1071, paragraph 7310.
Merck Manual, 15th Ed., p. 1502.
Merck Manual, 15th Ed., p. 1419.

*Primary Examiner*—Stanley J. Friedman
*Assistant Examiner*—Diane Gardner
*Attorney, Agent, or Firm*—Burton Rodney

[57] ABSTRACT

A new combination of drugs is provided which is formed of an angiotensin converting enzyme inhibitor such as ceranapril or captopril, and a dopaminergic receptor blocker which is preferably pimozide and a method for treating obsessive-compulsive disorder and also motor and phonic tics in Tourettes' syndrome using such combinations.

18 Claims, No Drawings

NEW COMBINATION AND METHOD FOR TREATING OBSESSIVE-COMPULSIVE DISORDER, AND MOTOR AND PHONIC TICS IN TOURETTES' SYNDROME USING SUCH COMBINATION

FIELD OF THE INVENTION

The present invention relates to a new combination of pharmaceuticals which is formed of an angiotensin converting enzyme inhibitor and a dopaminergic receptor blocker, which is preferably pimozide, and to a method for treating obsessive-compulsive disorder, and also motor and phonic tics in Tourettes' syndromes using such combination.

BACKGROUND OF THE INVENTION

Obsessive-compulsive neurosis is "a neurotic disorder characterized by the presence of recurrent ideas and fantasies and repetitive impulses or actions that the patient recognizes as morbid and toward which he feels a strong inner resistance." (Merck Manual, 15th Ed., p. 1505).

Tourettes' syndrome is a multiple tic disorder which "begins in childhood with simple tics but progresses to multiple, complex movements including respiratory and vocal tics." (Merck Manual, 15th Ed., p. 1419).

Pimozide, a known anti-psychotic has been suggested for use in treating both obsessive-compulsive neurosis and Tourettes' syndrome. However, it has been found that where sufficiently large amounts of pimozide are employed to produce a beneficial effect in treating the above disorders, significant side effects may be encountered. Thus, where amounts of pimozide greater than 0.04 mg/kg/day or greater than 2 mg per day, are employed over prolonged periods, tardive dyskinesia may result. Other side effects as a result of using pimozide include neuroleptic malignant syndrome (NMS), extrapyramidal reactions, neuromuscular reactions, impaired cognition and anticholinergic side effects.

Accordingly, a need exists for a drug or combination of drugs which may be used to treat obsessive-compulsive neurosis, and motor and phonic tics associated with Tourettes' syndrome which will not produce the untoward side effects normally resulting from use of therapeutic dosages of pimozide.

U.S. Pat. Nos. 4,046,889 and 4,105,776 to Ondetti et al. disclose proline derivatives, including captopril, which are angiotensin converting enzyme (ACE) inhibitors useful for treating hypertension.

U.S. Pat. No. 4,337,201 to Petrillo discloses phosphinylalkanoyl substituted prolines, including fosinopril, which are ACE inhibitors useful for treating hypertension.

U.S. Pat. No. 4,374,829 discloses carboxyalkyl dipeptide derivatives, including enalapril, which are ACE inhibitors useful for treating hypertension.

U.S. Pat. No. 4,452,790 to Karanewsky et al. discloses phosphonate substituted amino or imino acids and salts thereof and covers (S)-1-[6-amino-2-[[hydroxy(4-phenylbutyl)phosphinyl]-oxy]-1-oxohexyl]-L-proline (SQ 29,852, ceranapril). These compounds are ACE inhibitors useful in treating hypertension.

U.S. Pat. No. 4,316,906 to Ondetti et al. discloses ether and thioether mercaptoacyl prolines which are ACE inhibitors useful in treating hypertension. This Ondetti et al. patent covers zofenopril.

It is now believed that angiotensin converting enzyme inhibitors, especially mercapto containing ACE inhibitors such as captopril and zofenopril, when employed in combination with dopaminergic receptor blockers, such as pimozide, for treating obsessive-compulsive neurosis and Tourettes' syndrome are capable of reducing and, in some cases, preventing side effects resulting from use of the dopaminergic receptor blocker.

DESCRIPTION OF THE INVENTION

In accordance with the present invention, a new combination of drugs is provided which is used to treat obsessive-compulsive disorder, and motor and phonic tics in Tourettes' syndrome, which combination includes an angiotensin converting enzyme (ACE) inhibitor and a dopaminergic receptor blocker, which preferably is pimozide. The ACE inhibitor will be employed in a weight ratio to the dopaminergic receptor blocker of within the range of from about 5:1 to about 1000:1, and preferably from about 10:1 to about 800:1.

Further, in accordance with the present invention, a method is provided for treating obsessive-compulsive neurosis, and motor and phonic tics in Tourettes' syndrome, in a mammalian species, wherein a therapeutically effective amount of a combination of angiotensin converting enzyme inhibitor and dopaminergic receptor blocker is administered systemically, such as orally or parenterally.

In carrying out the method of the invention the dopaminergic receptor blocker preferably pimozide will be employed in amounts below that normally required to produce therapeutic results in the treatment of obsessive-compulsive neurosis and Tourettes' syndrome so that side effects such as tardive dyskinesia may be avoided. Thus, the combination of the invention will be administered to include a dosage of pimozide below 0.02 mg/kg per day, preferably below 0.01 mg/kg per day or less than 1 mg per day, preferably less than 0.8 mg per day, whichever is less. Even though less than therapeutic amounts of pimozide are employed the presence of the ACE inhibitor in conjunction therewith will produce therapeutic results without untoward side effects, such as tardive dyskinesia. In addition, the use of angiotensin converting enzyme inhibitor will allow slow withdrawal of the dopaminergic receptor blocker without emergence of neurological side effects.

The combination of the invention may be administered to hypertensive patients or normotensive patients in accordance with the methods of the present invention.

In preferred embodiments where the patient to be treated in accordance with the present invention is normotensive, the angiotensin converting enzyme inhibitor present in the combination of the invention may be administered in amounts below that required to cause hemodynamic effects, that is below that required to cause a reduction in blood pressure. Where the patient to be treated is hypertensive, then the angiotensin converting enzyme inhibitor present in the combination of the invention may be employed in amounts usually employed to treat hypertension.

The angiotensin converting enzyme inhibitor which may be employed herein preferably includes those containing a mercapto (—S—) moiety such as substituted proline derivatives, such as any of those disclosed in U.S. Pat. No. 4,046,889 to Ondetti et al. mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril, that is

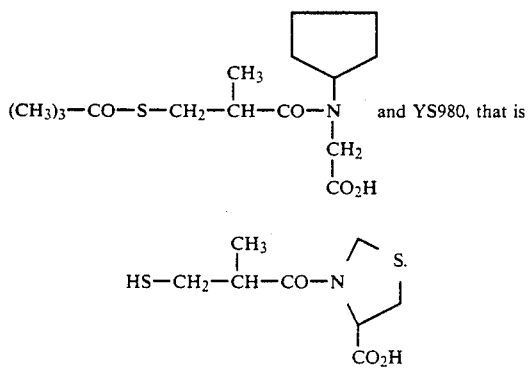

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)-phosphinyl]oxy]-1-oxohexyl]-L-proline (SQ 29,852 or ceranapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European patent Nos. 80822 and 60668; Chugai's MC-838 disclosed in CA. 102:72588v and Jap. J. Pharmacol. 40:373 (1986); Ciba-Geigy's CGS 14824 (3-([1-ethoxycarbonyl-3-phenyl-(1S)-propyl]-amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl-]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechst) disclosed in Eur. Patent No. 79-022 and Curr. Ther. Res. 40:74 (1986); Ru 44570 (Hoechst) disclosed in Arzneimittelforschung 35:1254 (1985), cilazapril (Hoffman-LaRoche) disclosed in J. Cardiovasc. Pharmacol. 9:39 (1987); $R_o$ 31-2201 (Hoffman-LaRoche) disclosed in FEBS Lett. 165:201 (1984); lisinopril (Merck) disclosed in Curr. Therap. Res. 37:342 (1985) and Eur. patent appl. No. 12-401, indalapril (delapril) disclosed in U. S. Patent No. 4,385,051; indolapril (Schering) disclosed in J. Cardiovasc. Pharmacol. 5:643, 655 (1983); spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344,949 and CI 925 (Warner-Lambert) ([3S-[2[R(*)R(*)]]3R(*)]-2-[2-[[1-(ethoxycarbonyl)-3-phenylpropyl]amino[-1-oxopropyl]-1,2,3,4-tetrahydro-6,7-dimethoxy-3-isoquinolinecarboxylic acid HCl) disclosed in Pharmacologist 26:243, 266 (1984), WY-44221 (Wyeth) disclosed in J. Med. Chem. 26:394 (1983).

Preferred are those ACE inhibitors which are proline or substituted proline derivatives such as captopril, zofenopril, fosinopril, ceranapril, enalapril or lisinopril.

The above-mentioned U.S. patents are incorporated herein by reference.

Examples of dopaminergic receptor blockers which may be employed herein include pimozide.

In carrying out the method of the present invention, the combination of the invention may be administered to mammalian species, namely, humans, and as such may be incorporated in a conventional systemic dosage form, such as a tablet, capsule, elixir or injectable, as well as suppository dosage forms that release ACE inhibitor and the dopaminergic receptor blocker in the bloodstream. The above dosage forms will also include the necessary carrier material, excipient, lubricant, buffer, bulking agent (such as mannitol), anti-oxidants (ascorbic acid of sodium bisulfite) or the like. Oral dosage forms are preferred, although parenteral forms such as intramuscular, intraperitoneal, or intravenous enema and suppository forms are quite satisfactory as well.

The dose administered must be carefully adjusted according to age, weight and condition of the patient, as well as the route of administration, dosage form and regimen and the desired result.

Thus, for oral administration, a satisfactory result may be obtained employing the ACE inhibitor in an amount within the range of from about 0.01 mg/kg/day to about 50 mg/kg/day and preferably from about 0.1 mg/kg/day to about 25 mg/kg/day and the dopaminergic receptor blocker, for example, pimozide in amounts less than 0.02 mg/kg/day, and preferably less than 0.01 mg/kg/day.

A preferred oral dosage form , such as tablets or capsules, will contain the ACE inhibitor in an amount of from about 0.1 to about 500 mg, preferably from about 2 to about 200 mg, and more preferably from about 3 to about 150 mg, and pimozide in an amount of from about 0.1 to about 1 mg and preferably from about 0.2 to about 0.8 mg.

For parenteral administration, the ACE inhibitor will be employed in an amount within the range of from about 0.005 mg/kg/day to about 10 mg/kg/day and preferably from about 0.01 mg/kg/day to about 1 mg/kg/day, and pimozide in an amount within the range of from about 0.05 to about 0.02 mg/kg/day and preferably from about 0.007 to about 0.01 mg/kg/day.

The composition described above may be administered in the dosage forms as described above in single or divided doses of one to four times daily. It may be advisable to start a patient on a low dose and work up gradually to a high dose.

Tablets of various sizes can be prepared, e.g., of about 5 to 700 mg in total weight, containing the active substance in the range described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending the active substance in a conventional liquid vehicle acceptable for pharmaceutical administration so as to provide the desired dosage in one to four teaspoonfuls.

Such dosage forms can be administered to the patient on a regimen of one to four doses per day.

Suppository formulations containing from about 5 to about 250 mg ACE inhibitor and 0.1 to 0.8 mg pimozide or other dopaminergic receptor blocker may be prepared as well using a conventional suppository base (such as disclosed in U.S. Pat. Nos. 4,344,968, 4,265,875, and 4,542,020) so as provide the desired dosage in one to four suppositories per day.

As indicated, where the patient to be treated is normotensive, then smaller amount of angiotensin converting enzyme inhibitor may be employed, that is below that required to reduce blood pressure. For example, for oral dosage forms, normotensives may be treated with from about 0.01 mg/kg to about 1 mg/kg or from about 1 mg to about 6 mg, one to four times daily.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

The formulations as described above will be administered for a prolonged period, that is, for as long as it is necessary to treat obsessive-compulsive neursis and/or motor and phonic tics of Tourettes' syndrome. Sustained release forms of such formulations which may provide such amounts biweekly, weekly, monthly and the like may also be employed. A dosing period of at least one to two weeks are required to achieve minimal benefit.

The following Examples represent preferred embodiments of the present invention.

EXAMPLE 1

A captopril-pimozide formulation suitable for oral administration in the treatment of obsessive-compulsive neurosis, and motor and phonic tics in Tourettes' syndrome is set out below.

1000 tablets each containing 100 mg of 1-[(2S)-3-mercapto-2-methylpropionyl]-L-proline and 0.5 mg of pimozide are produced from the following ingredients:

| | |
|---|---|
| 1-[(2S)-3-mercapto-2-methylpropionyl]-L-proline (captopril) | 100 g |
| Pimozide | 0.5 g |
| Corn starch | 50 g |
| Gelatin | 7.5 g |
| Avicel (microcrystalline cellulose) | 25 g |
| Magnesium stearate | 2.5 g |

The captopril, pimozide and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 5 mg of active ingredients which is used for treating obsessive-compulsive neurosis, and motor and phonic tics in Tourettes' syndrome.

EXAMPLE 2

By substituting 100 g of 1-(3-mercapto-2-D-methylpropanoyl)-L-proline for the captopril in Example 1, 1000 tablets each containing 100 mg of the 1-(3-mercapto-2-D-methylpropanoyl)-L-proline and 0.5 mg pimozide are produced which is useful in treating obsessive-compulsive neurosis, and motor and phonic tics in Tourettes' syndrome.

EXAMPLE 3

1000 tablets each containing 200 mg of captopril and 0.8 mg pimozide are produced from the following ingredients:

| | |
|---|---|
| Captopril | 200 g |
| Pimozide | 0.8 g |
| Lactose | 100 g |
| Avicel | 150 g |
| Corn starch | 50 g |
| Magnesium stearate | 5 g |

The captopril, pimozide, lactose and Avicel are admixed, then blended with the corn starch. Magnesium stearate is added. The dry mixture is compressed in a tablet press to form 1000 505 mg tablets each containing 200 mg of captopril and 0.8 mg of pimozide. The tablets are coated with a solution of Methocel E 15 (methyl cellulose) including as a color a lake containing yellow #6. The resulting tablets are useful in treating obsessive-compulsive neurosis, and motor and phonic tics in Tourettes' syndrome.

EXAMPLE 4

Two piece #1 gelatin capsules each containing 250 mg of enalapril and 0.7 mg of pimozide are filled with a mixture of the following ingredients:

| | |
|---|---|
| Captopril | 250 mg |
| Pimozide | 0.7 mg |
| Magnesium stearate | 7 mg |
| USP lactose | 193 mg |

The resulting capsules are useful in treating obsessive-compulsive neurosis, and motor and phonic tics in Tourettes' syndrome.

EXAMPLE 5

An injectable solution for use in treating obsessive-compulsive neurosis, and motor and phonic tics in Tourettes' syndrome is produced as follows:

| | |
|---|---|
| Captopril | 10 mg |
| Pimozide | 0.01 mg |
| Methyl paraben | 5 g |
| Propyl paraben | 1 g |
| Sodium chloride | 25 g |
| Water for injection qs. | 5 L. |

The captopril, pimozide, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 10 mg of captopril and 0.01 mg of pimozide per ml of solution for injection.

EXAMPLE 6

Tablets for use in treating obsessive-compulsive neurosis, and motor and phonic tics in Tourettes' syndrome are prepared following the procedure of Example 1 except that zofenopril is employed in place of captopril.

EXAMPLE 7

Tablets for use in treating obsessive-compulsive neurosis, and motor and phonic tics in Tourettes' syndrome are prepared following the procedure of Example 1 except that fosinopril is employed in place of captopril.

EXAMPLE 8

Tablets for use in treating obsessive-compulsive neurosis, and motor and phonic tics in Tourettes' syndrome are prepared following the procedure of Example 1 except that alacepril is employed in place of captopril.

EXAMPLE 9 AND 10

A suppository formulation containing conventional suppository base such as any of those disclosed in U.S. Pat. Nos. 4,344,968, 4,265,875 or 4,542,020, and N-(1-ethoxy-carbonyl-3-phenylpropyl)-L-alanyl-L-proline (40 mg), (enalapril) or captopril (25 mg), and 5 mg pimozide is prepared and is used to treat obsessive-compulsive neurosis, and motor and phonic tics in Tourettes' syndrome.

EXAMPLE 11

A modified release beadlet formulation capable of slowly releasing the angiotensin converting enzyme inhibitor captopril and pimozide over a period of up to 6 hours and having the following composition was prepared as described below.

| Ingredient | Amount in Parts by Weight |
|---|---|
| Captopril | 27 |
| Pimozide | 0.5 |
| Citric acid | 30 |
| Microcrystalline cellulose* | 43 |

*amount may vary to reflect chemical purity of captopril

The above ingredients were mixed and kneaded using water in a planetary mixer to form a wet mass. The wet mass was passed through a Nica E140 extruder to form an extrudate (~1 mm diameter). The extruder was then passed through a Nica spheronizer to form beadlets. The beadlets were then dried at 40° C. for 12-18 hours in a tray drying oven or for 2-4 hours in a fluid bed dryer. A fraction of the so-formed beadlets were filled into hard shell pharmaceutical capsules for use in obsessive-compulsive neurosis, and motor and phonic tics in Tourette's syndrome.

EXAMPLE 12

A modified release coated-beadlet formulation having the following composition was prepared as follows.

| | | | mg/dose |
|---|---|---|---|
| (i) | Core | | |
| | Captopril | | 5 mg |
| | Pimozide | | 0.1 mg |
| | Microcrystalline cellulose | | 159.1 mg |
| | Citric acid | | 37 mg |
| | Lactose | | 74.1 mg |
| (ii) | Sealcoat | | |
| | Hydroxypropyl methyl cellulose | ca. | 8.3 mg |
| | Polyethylene glycol | ca. | 2.8 mg |
| (iii) | Barriercoat | | |
| | Cellulose acetate phthalate | ca. | 4.2 mg |
| | Acetylated monoglycerides (Myvacet ® 9-40) | ca. | 1.3 mg |

The beadlet cores were prepared as described in Example 11. After the dried beadlets were formed, they were coated via a two step process as follows. An aqueous solution of hydroxypropyl methyl cellulose (7.5% by weight) and polyethylene glycol (2.5% by weight) was prepared and sprayed on to the beadlets to form a sealcoat. The beadlets were then coated with a barriercoat using an aqueous dispersion of cellulose acetate phthalate (30% by weight) mixed with acetylated monoglycerides (9.5% by weight). The beadlets were then filled into hard shell pharmaceutical capsules which are useful in treating obsessive-compulsive neurosis, and motor and phonic tics in Tourettes' syndrome.

What is claimed is:

1. A composition comprising an angiotensin converting enzyme inhibitor and a dopaminergic receptor blocker, employed in a weight ratio to each other of within the range of from about 5:1 to about 1000:1, wherein the dopaminergic receptor blocker is pimozide.

2. The composition as defined in claim 1 wherein the angiotensin converting enzyme inhibitor is employed in a weight ratio to the dopaminergic receptor blocker of within the range of from about 10:1 to 800:1.

3. The composition as defined in claim 1 wherein said angiotensin converting enzyme inhibitor is captopril.

4. The composition as defined in claim 1 wherein said angiotensin converting enzyme inhibitor is enalapril or lisinopril.

5. The composition as defined in claim 1 wherein said angiotensin converting enzyme inhibitor is selected from the group consisting of 1-[N-hydroxy(4-phenylbutyl)phosphinyl]-2-alanyl]-L-proline or its disolium salt (ceranapril), zofenopril and fosinopril.

6. The composition as defined in claim 1 wherein said angiotensin converting enzyme inhibitor is selected from the group consisting of captopril, enalapril, and lisinopril and the dopaminergic receptor blocker is pimozide.

7. A method for treating obsessive-compulsive neurosis in a mammalian specie, which comprises administering to a mammalian specie in need of such treatment an effective amount of a composition comprising an angiotensin converting enzyme inhibitor and dopaminergic receptor blocker, employed in a weight ratio to each other of within the range of from about 5:1 to about 1000:1, wherein said blocker is employed in an amount below that normally required to produce therapeutic results by itself, and wherein the dopaminergic receptor blocker is pimozide.

8. The method as defined in claim 7 wherein the angiotensin converting enzyme inhibitor is a mercapto containing ACE inhibitor.

9. The method as defined in claim 7 wherein said angiotensin converting enzyme inhibitor is employed in a weight ratio to the domaminergic receptor blocker of within the range of from about 5:1 to about 1000:1.

10. The method as defined in claim 7 wherein said angiotensin converting enzyme inhibitor is captopril.

11. The method as defined in claim 7 wherein said angiotensin converting enzyme inhibitor is selected from the group consisting of fentiapril, ceranapril, fosinopril, zofenopril, enalapril, and lisinopril, and the dopaminergic receptor blocker is pimozide.

12. The method as defined in claim 7 wherein said angiotensin converting enzyme inhibitor is administered in single or divided doses of from about 0.1 to about 500 mg/one to four times daily and the dopaminergic receptor blocker which is pimozide is employed to provide less than about 1 mg per day total.

13. A method of treating motor and phonic tics of Tourette's syndrome in a mammalian specie, which comprises administering to a mammalian specie in need of such treatment an effective amount of a composition comprising an angiotensin converting enzyme inhibitor and dopaminergic receptor blocker, employed in a weight ratio to each other of from about 5:1 to about 1000:1, wherein said blocker is employed in an amount below that normally required to produce therapeutic results by itself, and wherein the dopaminergic receptor blocker is pimozide.

14. The method as defined as in claim 13 wherein the angiotensin converting enzyme inhibitor is a mercapto containing ACE inhibitor.

15. The method as defined in claim 12 wherein said angiotensin converting enzyme inhibitor is employed in a weight ratio to the dopaminergic receptor blocker of within the range of from about 5:1 to about 1000:1.

16. The method as defined in claim 15 wherein said angiotensin converting enzyme inhibitor is capopril.

17. The method as defined in claim 15 wherein said angiotensin converting enzyme inhibitor is selected from the group consisting of fentiapril, ceranapril, fosinopril, zofenopril, enalapril, and lisinopril, and the dopaminergic receptor blocker is pimozide.

18. The method as defined in claim 15 wherein said angiotensin converting enzyme inhibitor is administered in single or divided doses of from about 0.1 to about 500 mg/one to four times daily and the dopaminergic receptor blocker which is pimozide is employed to provide less than about 1 mg per day total.

* * * * *

UNITED STATES PATENT AND TRADEMARK OFFICE
CERTIFICATE OF CORRECTION

PATENT NO. : 5,030,648
DATED : July 9, 1991
INVENTOR(S) : Abraham Sudilovsky

It is certified that error appears in the above-identified patent and that said Letters Patent is hereby corrected as shown below:

Column 8, line 59, please change "disolium" to --disodium--.

Column 9, line 14, please change "domaminergic " to --dopaminergic--.

Signed and Sealed this

Fifteenth Day of December, 1992

Attest:

DOUGLAS B. COMER

*Attesting Officer*     *Acting Commissioner of Patents and Trademarks*